United States Patent [19]

Hanzawa et al.

[11] 3,942,767
[45] Mar. 9, 1976

[54] METHOD AND APPARATUS FOR CONTINUOUSLY AUTOMATICALLY CONTROLLING THE WATER CONTENT OF KNEADED VISCOUS MATERIALS

[75] Inventors: Keiji Hanzawa, Sapporo; Yoshiyuki Takahashi, Aikawa; Nobuyoshi Suga, Kawasaki; Tojo Kato, Atsugi; Makoto Handa; Hiromichi Hayashi, both of Sapporo; Shinichi Taneya; Toshimaro Sone, both of Tokyo, all of Japan

[73] Assignees: Snow Brand Milk Products Co., Ltd., Hokkaido; Anritsu Electric Co., Ltd., Tokyo, both of Japan

[22] Filed: Feb. 4, 1974

[21] Appl. No.: 439,636

Related U.S. Application Data

[62] Division of Ser. No. 264,570, June 20, 1972, Pat. No. 3,841,610.

[30] Foreign Application Priority Data
Aug. 25, 1971 Japan................................ 46-65006
Aug. 25, 1971 Japan................................ 46-65007

[52] U.S. Cl..................... 259/7; 259/191; 259/149
[51] Int. Cl.²........................................... B01F 3/10
[58] Field of Search........... 259/149, 154, 191, 7, 9, 259/10

[56] References Cited
UNITED STATES PATENTS
3,353,270   11/1967   Simon............................... 99/462 X
3,519,252   7/1970   Dietert............................... 259/149

Primary Examiner—Harvey C. Hornsby
Assistant Examiner—Alan Cantor
Attorney, Agent, or Firm—Stevens, Davis, Miller & Mosher

[57] ABSTRACT

A feed material is introduced into a pressure-kneading portion of a kneader with a slightly insufficient water content, wherein the remaining water is added and the material is kneaded to be delivered from the kneader as having a predetermined water content, and concurrently the water content of the kneaded material being delivered is continuously measured near the exit of said kneader and the amount of water to be added to the pressure-kneading portion is controlled according to the measured water content, whereby the water content in the kneaded material is maintained constant.

1 Claim, 6 Drawing Figures

METHOD AND APPARATUS FOR CONTINUOUSLY AUTOMATICALLY CONTROLLING THE WATER CONTENT OF KNEADED VISCOUS MATERIALS

This is a division of application Ser. No. 264,570, filed June 20, 1972 now U.S. Pat. No. 3,841,610 issued Oct. 15, 1974.

This invention relates to a method of and an apparatus for continuously automatically controlling the water content of kneaded viscous materials, such as butter and margarin, though not limitative, in the production of said kneaded materials. Further, the invention relates to an electrode plate adapted for use in controlling the water content of kneaded materials.

In general, in an apparatus for continuously producing kneaded materials, such as butter and margarin, a cream is introduced continuously into a pressure-kneading portion of the apparatus, wherein a suitable quantity of water is added, and then extruded from a nozzle. In order to determine the quantity of water to be added, it is necessary to know the water content in the product. The water content in the product has heretofore been measured by a non-continuous method, i.e. by sampling, but this method not only requires a skill but also causes a time lag in adjusting the quantity of water in accordance with the measured value. It has the additional disadvantage that the adjustment cannot be effected accurately and quickly as it is performed manually.

Therefore, an object of the present invention is to provide a method of continuously automatically controlling the water content of a kneaded viscous material, which comprises introducing a feed material into a pressure-kneading portion of a kneader with a slightly insufficient water content, adding the remaining water to said material being kneaded in said pressure-kneading portion to increase the water content to a predetermined level, discharging the kneaded material from the kneader, continuously measuring the water content of the kneaded material being discharged near the exit of said kneader and automatically controlling the quantity of water to be added to the pressure-kneading portion in accordance with the measured value, thereby maintaining the water contained in the kneaded material constant.

Another object of the invention is to provide an apparatus for continuously automatically controlling the water content of a kneaded material, which comprises a kneader having a pressure-kneading portion for kneading a feed material therein and a nozzle portion connected to said pressure-kneading portion for discharging the kneaded feed material therethrough as a kneaded material, water adding means connected to said pressure-kneading portion and including a water pump capable of supplying water in a varying quantity, water content detecting means arranged in said nozzle portion and including electrodes for detecting the water content of the kneaded material being extruded through said nozzle upon measuring the electric capacity thereof, and means for controlling the quantity of water supplied from said water pump in accordance with the detected water content to maintain the quantity of water contained in the kneaded material constant.

For measuring the electric capacity of a kneaded viscous material to determine the water content thereof, a pair of planar electrode plates have been used which are spaced apart from each other in opposed relation. The electric capacity of the material is measured by passing it between the electrode plates, and the water content thereof is determined from the measured electric capacity. The electrodes of this type can be effectively used in the continuous, automatic control method and apparatus of the present invention described above, but has some disadvantages.

First of all, when the conventional electrodes as mentioned above are applied to the measurement of the water content of a highly viscous material, such as butter or margarin, the material is subjected to a large shearing force from the electrode plates which causes the water to be separated from the material, possibly resulting in a demulsification of the product and an measurement error. Further, since these prior art electrodes are not of water-proof structure, the water carried in the highly viscous material and containing electrolytes, such as salt (sodium chloride), occasionally causes shorting of the electrodes. Furthermore, when such electrodes are used in the production of butter or margarin, the water contained in the material tends to condense on the electrodes, providing a cause of measurement error, and in addition, the sterilization and cleaning of the electrodes are impossible.

Therefore, still another object of the present invention is to provide an electrode plate for use in the measurement of the water content of a viscous material, which comprises a single sheet of a substrate plate made of an electric insulator, a pair of electrodes printed on said substrate plate and a thin layer of an electric insulator covering said printed electrodes, said viscous material being moved over said thin layer, whereby the electric capacity thereof is measured by said electrode plate.

A further object of the invention is to provide an electrode plate for use in the measurement of the water content of a viscous material of the character described above, which is disposed in a frame with said electrically insulating thin layer exposed on the upper side of said frame and with a filler disposed therebelow, and completely hermetically sealed in said frame with a sealing material filling the gaps within said frame.

In the construction of the electrode plate according to the present invention, it is preferable that the electrodes each have a pectinate shape and are arranged with each tooth of one electrode received between adjacent teeth of the other electrode. Alternatively, the electrodes may be formed each in a U-shape and arranged in opposed relation with their legs in alternate positions. Still alternatively, the electrodes may be formed in a helical shape or any other shape. With the electrode plate of the invention, arcuate lines of electric force are generated extending from one electrode to the other one in the thicknesswise direction of the material to be measured through said material, by which the electric capacity and hence the water content of the material is measured. The space interval between the electrodes must be suitably selected according to the thickness of the material to be measured, because the lengths of the lines of electric force passing through the material become shorter as the interval between the electrodes becomes smaller.

Embodiments of the present invention will be described hereunder with reference to the accompanying drawings.

Figure 1:
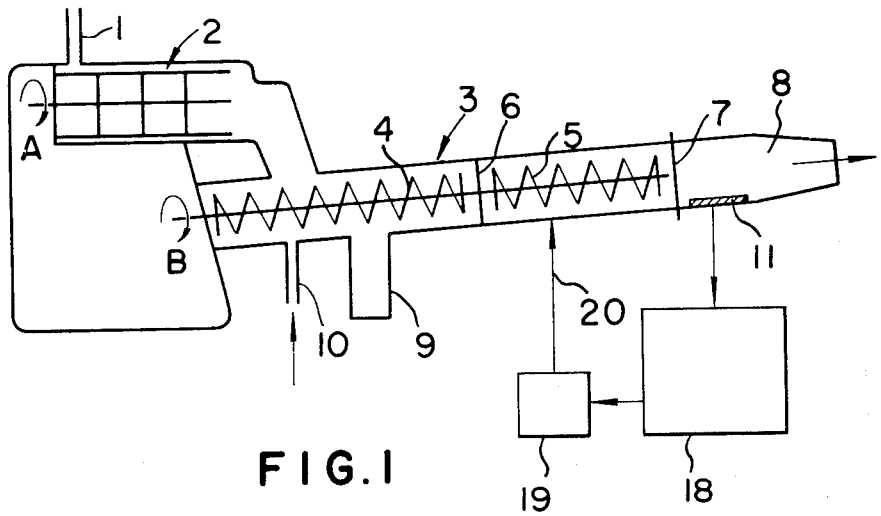
FIG. 1 is a schematic sectional view showing an embodiment of the present invention.

With reference to FIG. 1, a continuous butter making machine to which the method of this invention is applied has a starting cream inlet 1 and a churning mechanism 2. The churning mechanism is driven from a suitable drive source in the direction of the arrow A. Reference numeral 3 generally designates a pressure-kneading portion which is provided therein kneading and conveying screws 4, 5. These screws 4, 5 are driven also from a suitable drive source in the direction of the arrow B. A nozzle 8 is provided at the forward end of the pressure-kneading portion 3. Reference numerals 6, 7 designate screens disposed in the path of travel of the butter being conveyed by the screws 4, 5, 9 designates a container of butter milk and 10 designates a washing water inlet. The arrangement described above is already known as a continuous butter making machine, and reference may be made, for example, to the construction of the Contimab type apparatus produced and sold by Ets Simon Freres in France. In the arrangement described above, the starting cream fed from the inlet 1 is subjected to churning by the churning mechanism 2 and introduced into the pressure-kneading portion 3. The churned butter granules in the pressure-kneading portion 3 are washed with water supplied thereto from the washing water inlet 10, conveyed by the screws 4, 5 while being kneaded by said screws, and discharged from the nozzle 8 as the product butter.

In the present invention, an electrode plate 11 is provided in the nozzle portion 8 for continuously measuring the water content of the butter being discharged from the nozzle 8.

This electrode plate 11 is of the construction which will be described later, and connected to a control apparatus indicated at 18 in FIG. 1. The control apparatus 18 is operative in such a manner that it detects a variation of the electric capacity of the butter by the arcuate electric field formed across electrodes of the electrode plate and generates a signal representative of the detected electric capacity variation, which is supplied to motor-driven water pump 19 to control the quantity of water to be supplied from a water supply port 20.

Figure 2:
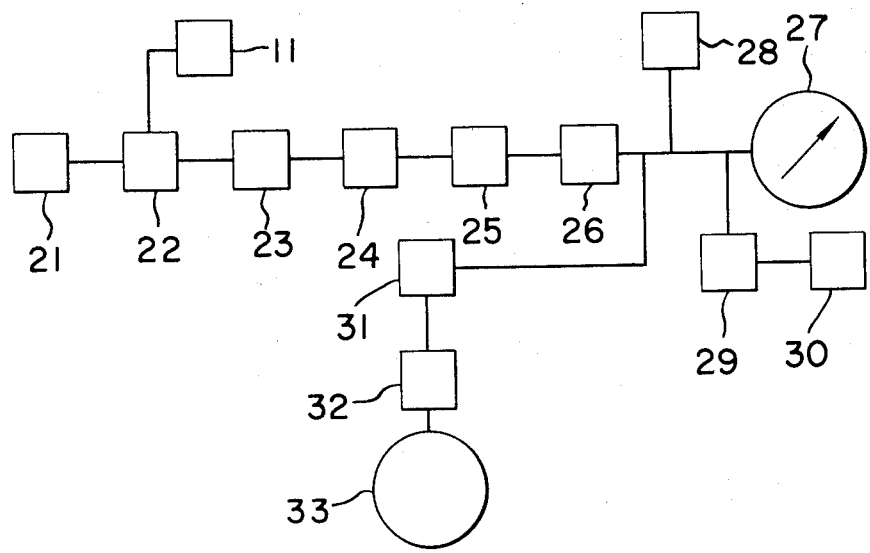
FIG. 2 is a block diagram showing an example of the control apparatus.

FIG. 2 is a block diagram showing an embodiment of the control apparatus 18. In FIG. 2, reference numeral 21 designates an oscillator and 22 designates a transformer bridge to which the electrode plate 11 is connected. The bridge 22 is connected to an indicator 27 through an alternating current amplifier 23, a detector 24, a parallel shifting circuit 25 and a high-cut circuit 26, and also connected to a recorder 28 as required. The output of the high-cut circuit 26 is supplied through a direct current amplifier 31 to a motor 32 to control the rotation of a pump 33. Reference numeral 29 designates a limit signal generating circuit and 30 designates an alarm.

Figure 3:
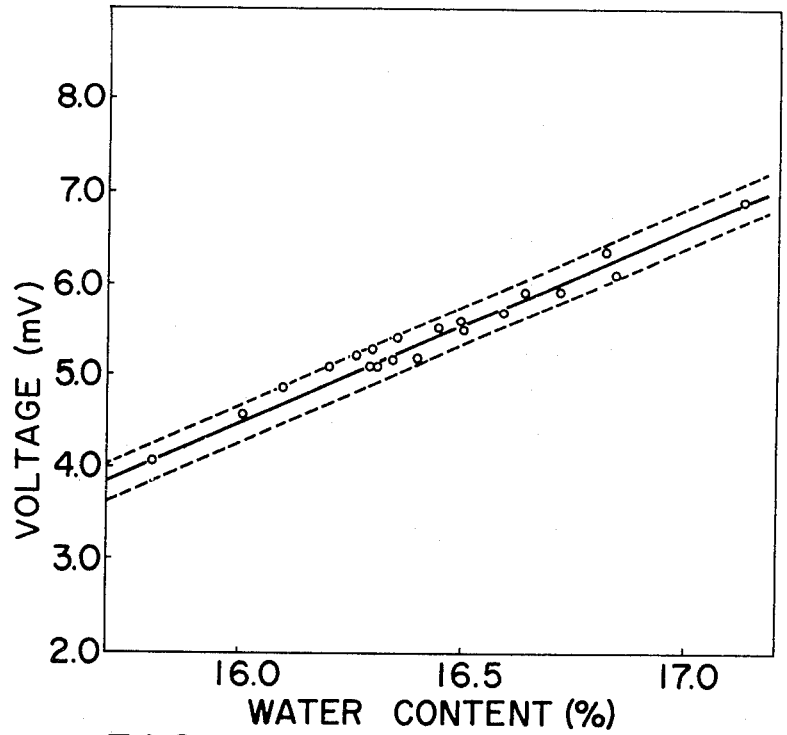
FIG. 3 is a graph showing the relationship between the voltage and the actual water content.

Namely, in the apparatus for practising the method of this invention water is added to the product from the water inlet 20, but the water content of the product being discharged from the nozzle 8 is continuously measured and the quantity of water added from the water inlet 20 is controlled according to the measured water content, whereby the water content of the product is automatically maintained at the optimum level. The oscillator 21 is of 50 K – 3 MHz, preferably of 300 KHz. It was found through experiment that the voltage and the actual water content are in substantially proportional relation to each other as shown in FIG. 3. FIG. 3 shows the result of the experiment conducted with the Contimab type machine under such conditions that the cream temperature was 11°C., the fat content in the cream was 41.5%, the speed of a churning cylinder (barattage) was 1400 RPM and the speed of a working chamber (malaxage) was 48 – 68 RPM.

Figure 4:
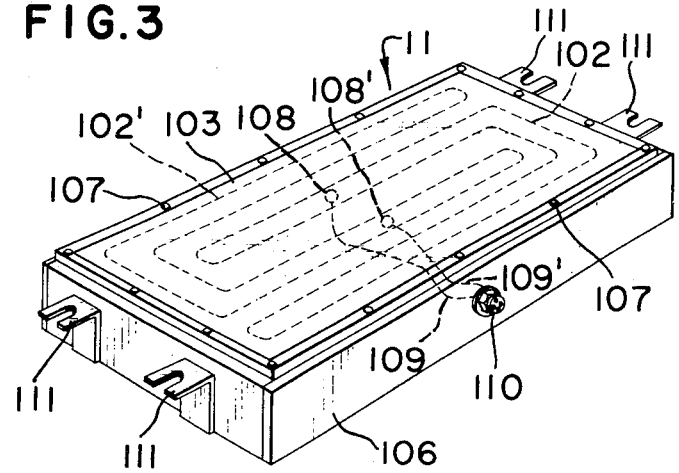
FIG. 4 is a perspective view of an embodiment of the electrode plate according to the invention.
Figure 5:
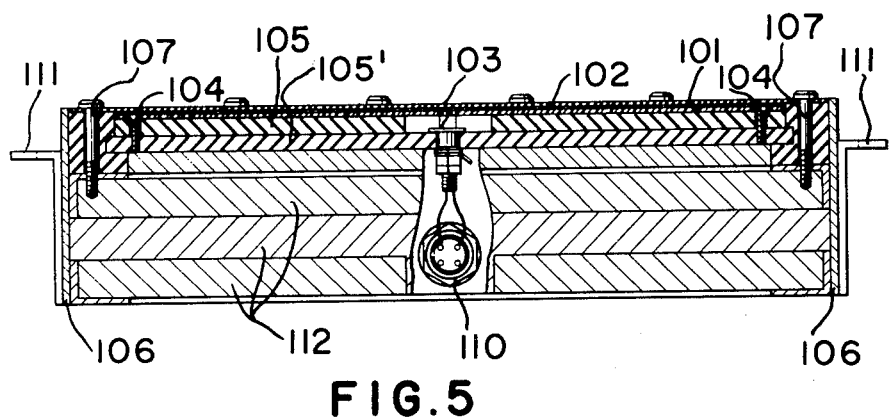
FIG. 5 is a sectional view of the electrode plate shown in FIG. 4.

The electrode plate suitably used in the method and apparatus of this invention will be described hereunder:

With reference to FIGS. 4 and 5, reference numeral 101 designates a substrate plate consisting of an epoxy resin-coated glass fiber cloth, on which electrodes 102, 102' consisting, for example, of copper foil are printed each in a substantially U-shape. Further, the surface of the substrate plate 101 is coated with a layer of an electric insulator, such as plastics, and thus the electrodes 102, 102' are completely insulated against the exterior. In this embodiment, the substrate plate 101 is placed on and secured to insulating plates 105, 105' by means of screws 104 in juxtaposed relation, and the resultant laminate is disposed, for example, in a stainless steel frame 106 and secured therein by means of screws 107. Reference numerals 108, 108' designate through-holes formed in the substrate plate 101 and conductors 109, 109' are extended through said through-holes 108, 108' respectively, with one ends thereof connected to the electrodes 102, 102' and the other ends to a socket 110 which in turn is connected to the control apparatus 18 shown in FIG. 1. Reference numeral 111 designates fittings provided on the frame 106. The space beneath the insulating plates 105, 105' is filled with a filler 112, such as a resin material, and the gaps within the frame 106 are filled with a sealing compound, so that the electrode plate is completely hermetically sealed.

Figure 6:
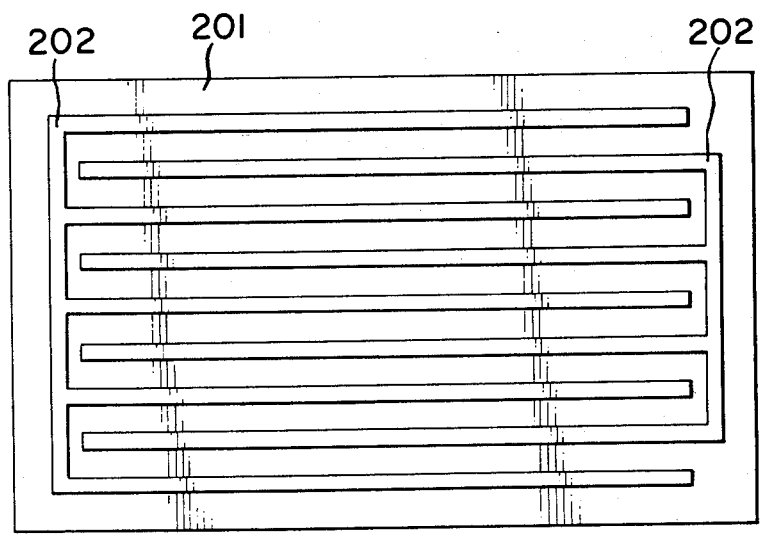
FIG. 6 is a plan view of another embodiment of the electrode plate according to the invention.

Another form of the electrode plate is shown in FIG. 6. In this form, electrodes 202, 202' are printed on an electrically insulating substrate plate 201, each in a pectinate shape. It should be understood that, according to the present invention, the electrodes to be printed on the substrate plate may be of any other shape.

With the electrode plate of the construction described above, a material to be measured is continuously moved along the upper surface of the insulating coating layer 103 and, during this period, the socket 110 is connected to the control apparatus 18 shown in FIG. 1, whereby an electric field is formed across the electrodes 102, 102' or 202, 202' and the electric capacity of the material is measured. Thus, the water content of the material can be continuously measured from the measured electric capacity thereof. According to the invention, the material to be measured is not subjected to a large shearing force since it is not compressed between a pair of electrodes during movement, and further the washing with water and sterilization of the electrode plate become possible since it can be completely sealed hermetically. For the same reason, shorting of the electrodes can be prevented which otherwise occurs by contact with water containing electrolytes such as salt (sodium chloride), and further the measurement error can be minimized.

What is claimed is:

1. A method of continuously automatically controlling the water content of a kneaded viscous material, comprising introducing a feed material into a pressure-kneading portion of a kneader with a slightly insufficient water content, adding salt-free water to said material being kneaded in said pressure-kneading portion to increase the water content to a predetermined level, discharging the kneaded material from the kneader, continuously measuring the water content of the kneaded material being discharged near the exist of said kneader and automatically controlling the quantity of salt-free water to be added to the pressure-kneading portion in accordance with the measured value, thereby to maintain the water contained in the kneaded material constant.

* * * * *